United States Patent [19]

Atala et al.

[11] Patent Number: 5,411,475
[45] Date of Patent: * May 2, 1995

[54] DIRECTLY VISUALIZED METHOD FOR DEPLOYING A DETACHABLE BALLOON AT A TARGET SITE IN VIVO

[75] Inventors: Anthony Atala, Newton; James Mandell, Brookline, both of Mass.

[73] Assignee: Children's Medical Center Corporation, Boston, Mass.

[*] Notice: The portion of the term of this patent subsequent to Apr. 19, 2011 has been disclaimed.

[21] Appl. No.: 54,375

[22] Filed: Apr. 28, 1993

Related U.S. Application Data

[63] Continuation-in-part of Ser. No. 782,058, Oct. 24, 1991, Pat. No. 5,304,123.

[51] Int. Cl.$^6$ ............................................. A61M 29/02
[52] U.S. Cl. ................................. 604/54; 606/192; 604/96
[58] Field of Search ............... 606/108, 192, 194, 191, 606/195; 604/96, 54; 623/1, 12; 128/898

[56] References Cited

U.S. PATENT DOCUMENTS

| | | |
|---|---|---|
| 3,831,585 | 8/1974 | Haber et al. |
| 4,282,875 | 8/1981 | Serbinenko et al. |
| 4,311,146 | 1/1982 | Wonder. |
| 4,327,734 | 5/1982 | White, Jr. |
| 4,334,327 | 6/1982 | Lyman et al. |
| 4,341,218 | 7/1982 | Ü. |
| 4,346,712 | 8/1982 | Handa et al. |
| 4,364,392 | 12/1982 | Strother et al. |
| 4,402,319 | 9/1983 | Handa et al. |
| 4,441,495 | 4/1984 | Hicswa. |
| 4,517,979 | 5/1985 | Pecenica. |
| 4,520,823 | 6/1985 | LeVeen et al. |
| 4,545,367 | 10/1985 | Tucci. |
| 4,773,393 | 8/1986 | Haber et al. |
| 4,802,479 | 2/1989 | Haber et al. |
| 4,832,680 | 5/1989 | Haber et al. |
| 5,007,898 | 4/1991 | Rosenbluth et al. |
| 5,078,681 | 1/1992 | Kawashima ........................... 604/53 |

FOREIGN PATENT DOCUMENTS 2185400 7/1987 United Kingdom.

OTHER PUBLICATIONS

Atala et al., "Management of Primary Vesicoureteral Reflux", *Infections in Urology*, Mar./Apr. 1990, pp. 39–43.

Reproduction of Figures from several textbooks depicting various surgical procedures used to treat vesicoureteral reflux (4 sheets total).

*Primary Examiner*—Ren Yan
*Attorney, Agent, or Firm*—Thomas J. Engellenner; Elizabeth A. Hanley; Lahive & Cockfield

[57] ABSTRACT

A directly visualized method for deploying a detachable balloon to a target site in vivo is described. The method allows a physician or technician to deploy the detachable balloon to the target site while directly visualizing the detachment of the balloon and/or the effects of the detached balloon on the target site in vivo. The present invention alleviates problems associated with the use of indirect visualization techniques conventionally used for deploying such detachable balloons. The directly, visualized method of this invention includes the steps of providing a scope capable of directly visualizing a target site in vivo, passing a balloon catheter including an uninflated, detachable balloon through the lumen of a positioning element of the scope, and inflating and detaching the balloon at the target site in vivo.

21 Claims, 3 Drawing Sheets

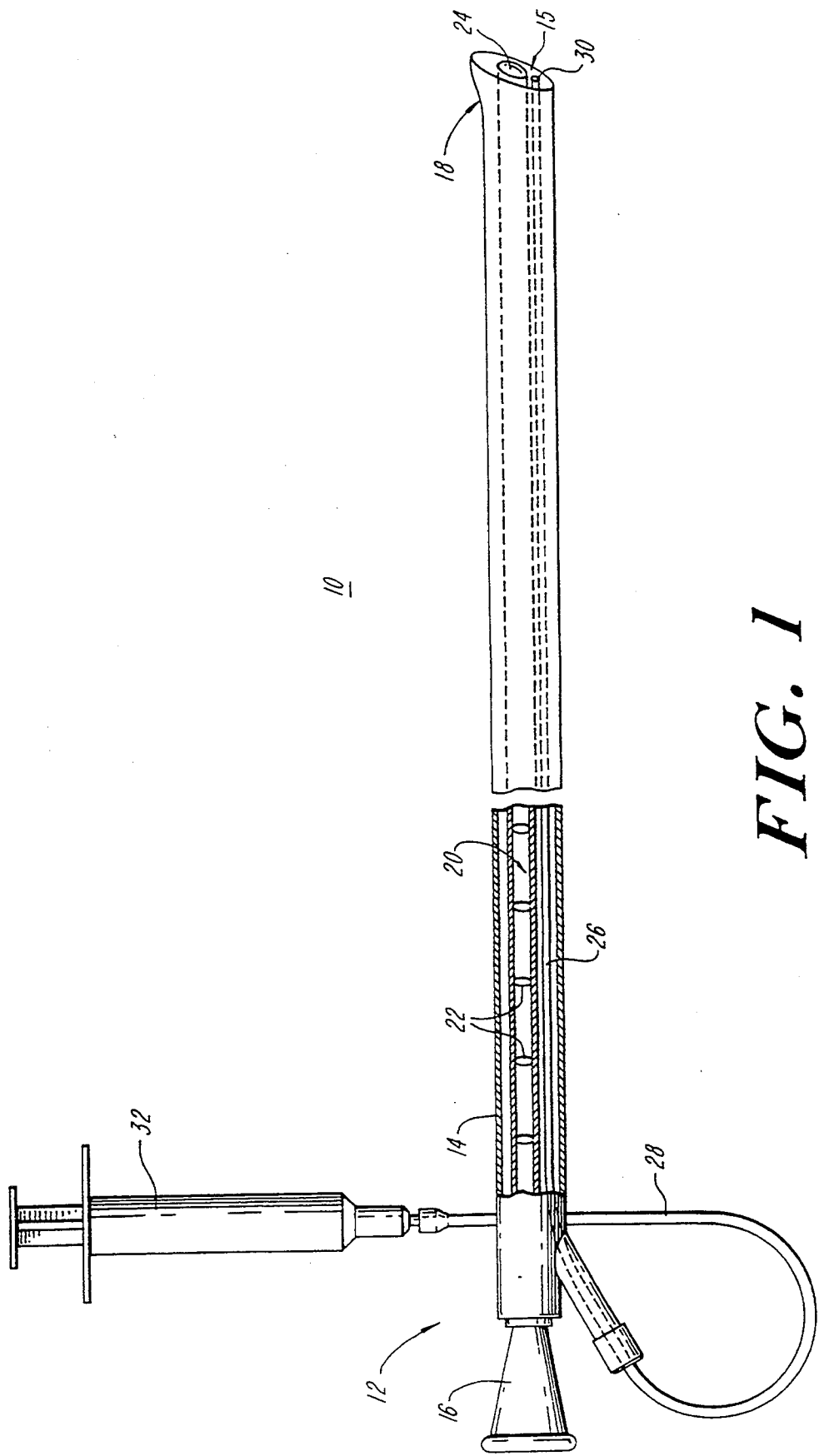

DIRECTLY VISUALIZED METHOD FOR DEPLOYING A DETACHABLE BALLOON AT A TARGET SITE IN VIVO

RELATED APPLICATION

This application is a continuation-in-part application of Ser. No. 07/782,058 entitled DETACHABLE BALLOON SYSTEM FOR ENDOSCOPIC TREATMENT OF VESICOURETERAL REFLUX filed on Oct. 24, 1991, now U.S. Pat. No. 5,304,123 the contents of which are expressly incorporated by reference.

BACKGROUND OF THE INVENTION

The use of balloon catheters is prevalent in medical procedures involving blood vessels, body cavities, and the like. Balloon catheters carrying a detachable balloon portion also have been previously described and have been used extensively in the cardiovascular area. The balloon catheters may be used to occlude vessels in certain types of cardiovascular surgery or further may be used to expand a blood vessel such as in angioplasty.

Detachable balloons also have been used to treat urinary incontinence (see Haber et al., U.S. Pat. Nos. 4,832,680, issued May 23, 1989; U.S. Pat. No. 4,802,479, issued Feb. 7, 1989; and U.S. Pat. No. 4,773,393, issued Feb. 27, 1988). Haber et al. describe an extensible, inflatable containment membrane which is implanted between the urethra and the subcutaneous corpus spongiousum of a patient to overcome urinary incontinence. The containment membrane of Haber et al. is positioned using a hypodermic needle, however, the balloon does not pass through the lumen of the hypodermic needle. Haber et al. developed specialized instrumentation to accommodate the positioning and insertion of their containment membrane. Haber et al. further do not mention the use of a scope in conjunction with their device.

SUMMARY OF THE INVENTION

The present invention provides a directly visualized method for deploying a detachable balloon to a target site in vivo. The method of this invention allows a physician or technician to deploy a detachable balloon to a target site while directly visualizing the detachment of the balloon and/or the effects of the detached balloon on the target site in vivo. The present invention alleviates problems associated with the use of indirect visualization techniques conventionally used for deploying such detachable balloons. The methods of the present invention include the treatment of vesicoureteral reflux, methods for birth control, and methods of treating urinary incontinence.

The directly visualized method of this invention includes the provision of a scope capable of directly visualizing a target site in vivo. A balloon catheter (including an uninflated, detachable balloon) is passed through the lumen of a positioning element of the scope. The balloon is inflated and detached at the target site in vivo.

The present invention also pertains to a system for deploying a detachable balloon to a target site in vivo which is further capable of directly visualizing the detached inflated balloon and/or its effects in vivo. The system includes a scope having a positioning element and a balloon catheter. The balloon catheter includes an uninflated, detachable balloon including a valve mechanism. The uninflated, detachable balloon has a sufficiently small diameter allowing it to pass through a lumen of the positioning element, e.g. a hypodermic needle.

BRIEF DESCRIPTION OF THE DRAWINGS

FIG. 1 is schematic diagram of a system according to the invention;

DETAILED DESCRIPTION

Figure 2A:
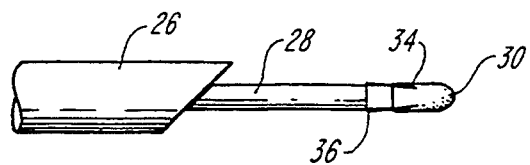
FIG. 2A is a more detailed schematic diagram of the distal tip of the system of FIG. 1 prior to inflation of the balloon.

The present invention pertains to a directly visualized method for deploying a detachable balloon to a target site in vivo. The method involves the passing of a balloon catheter through a lumen of a positioning element of a scope and the subsequent inflation and detachment of the balloon portion of the catheter.

The target site can be a site selected such that the implantation of a detachable balloon would be advantageous to a subject. The target site, for example, can be in close proximity to or within a duct and the purpose of the implantation of the detachable balloon is to block the duct from within or provide external pressure causing partial or complete closure of the duct. For example, the target site may be the subureteral region of a reflux-prone bladder as described in detail below.

The method of this invention further provides a means for birth control. For example, the target site can be within a female subject's fallopian tube(s) thereby preventing an egg from being fertilized by a sperm. Alternatively, the fallopian tube can be blocked by placing the inflated, detached balloon external to the fallopian tube in a manner which provides occlusive pressure to the fallopian tube(s) resulting in closure.

The method of this invention also can be used as a form of birth control by blocking the appropriate ducts of a male subject. For example, the vas deferens or another duct involved in the delivery of sperm may be blocked by implanting the inflated, detached balloon within the duct (causing blockage) or external to the duct in a manner which results in closure of the duct. Thus, the present invention provides an alternative to the conventional vasectomy.

The method of this invention also can be used as a means for treating urinary incontinence (see Haber et al., cited Supra, the contents of each of U.S. Pat. Nos. 4,832,680; 4,802,479; and 4,773,393, are expressly incorporated by reference herein). The inflated, detached balloon can be placed between the urethra and the subcutaneous corpus spongiousum providing a localized, controlled tissue volume increase. The corpus spongiousum would be expanded thereby occluding the urethra.

It should be understood that one of ordinary skill in the art would be able to envision other target sites within a subject which would be appropriate target sites for the present invention. The preferred target sites are target sites located in close proximity to or within a duct.

The scope of the present invention can be any scope capable of providing direct visualization of a target site. Examples of scopes which are intended to be encompassed by the present invention are endoscopes such as cystoscopes. Various cystoscopes can be used in the present invention and are commercially available from various sources including, for example, Karl Storz Co. (Culver, Calif.); and Olympus Corporation of (Wilmington, Mass.). Direct visualization is intended to encompass visualization by the human eye or visualization using a media which is an actual picture of what would be seen by the human eye looking through the scope, e.g. video.

The positioning element of the present invention can be an element capable of positioning the detachable balloon at the selected target site in vivo. The positioning element typically extends longitudinally through the scope and has a lumen extending longitudinally therethrough. The lumen of the positioning element preferably has an inside diameter of less than about 0.036 inches. An example of a type of positioning element is a hypodermic needle. The positioning element useful in establishing a subureteral pocket can be a cystoscopic needle, e.g., a 19 gauge needle which is small enough to fit within standard cystoscopic equipment. In one system, a thin walled cystoscopic needle was obtained from Cook Urological Co. (Spencer, Ind.) which had a 19 gauge outer diameter but had the inner diameter of a standard 18 gauge needle (0.036 inches).

Balloon structures useful in the present invention can be formed from silicone or similar substantially nonantigenic elastic materials. The uninflated balloons preferably are sized to fit unto the tip of a catheter which can pass readily through the lumen of the positioning device (e.g., a cystoscopic needle).

The balloon structures can take various forms but preferably include a sealing mechanism which seals the balloon upon inflation. The sealing mechanism can be achieved, for example, by a constrictive collar, or a lip seal, or both.

The balloon can be delivered by a catheter which is inserted through the needle or positioning means to the site where the balloon is to be inflated. In one preferred embodiment, the catheter provides a means for not only inflating the balloon but also means for filling the balloon with a biocompatible material. Catheters suitable for use in the present invention are available from various sources including, for example, Interventional Therapeutics (San Francisco, Calif.).

Various materials can be used to fill the balloon, including collagen, autologous fat or cellular extracts, or an inert polymer. In one embodiment, the balloon is filled with a polymerizable solution, such as an acrylic solution which solidifies in situ. In a preferred embodiment, the polymerizable solution is a solution of hydroxyethyl methylacrylate (HEMA) which is cured to a solid form by the addition of ferrous sulfate and hydrogen peroxide.

The invention will next be described in connection with certain illustrated embodiments; however, it should be clear that those skilled in the art can make various modifications, additions and subtractions without departing from the spirit or scope of the invention. For example, although the invention is specifically described in connection with the treatment or vesicoureteral reflux, it should be clear that the invention is applicable to other treatment protocols.

FIG. 1 shows a system 10 for treatment of vesicoureteral reflux including a cystoscope 12 having a outer sheath 14 and an inner lumen 15. The cystoscope includes an eyepiece or other viewing port (e.g., a video adaptor) 16 in optical communication with the distal tip 18 of the cystoscope. In the illustrated embodiment, an optical relay mechanism 20, including for example, a series of lenslets 22 and a distal cystoscopic lens 24 are disposed within the lumen 15 of the cystoscope 12.

The cystoscope 12 further includes a positioning means, e.g., a cystoscopic needle 26 for positioning a balloon structure 30 in the subureteral region of a refluxing bladder. The balloon structure is preferably connected to a catheter 28 which passes through the positioning means 26 and serves to inflate the balloon structure. In the illustrated embodiment, the catheter is connected to a polymerizable solution supply, e.g., a syringe 32.

Figure 2B:
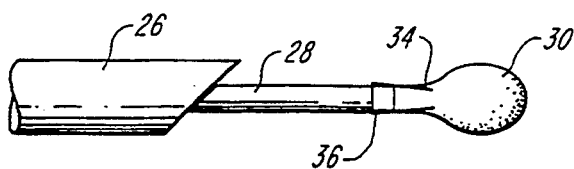
FIG. 2B is another diagram of the system of FIG. 2A in which the balloon means is being inflated.
Figure 2C:
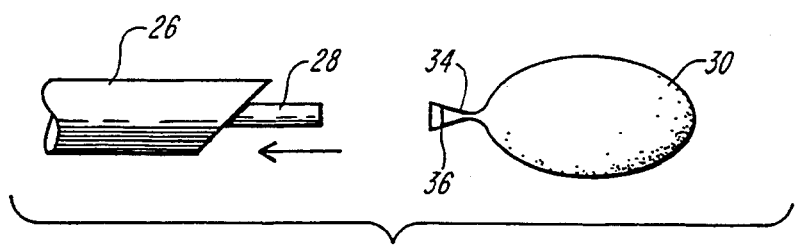
FIG. 2C is another diagram of the system of FIG. 2B in which an inflated balloon means has been detached.

In FIGS. 2A-2C, the operation of the positioning means 26 and the balloon structure 30 is illustrated in more detail. As shown in FIG. 2A, the end of cystoscopic needle 26 is positioned at a site where inflation and implantation of the balloon structure is desired. Catheter 28 with balloon 30 at its tip is then advanced through the needle 26 into place at the site, e.g. in the subureteral region, and then inflated as shown in FIG. 2B.

The balloon structure 30 preferably includes at least one sealing mechanism, such a lip or flap seal 34 or a constrictive collar 36, which provide for self-sealing of the balloon means upon inflation. Such sealing mechanisms operate to expel and/or close the balloon when a certain inflation state is reached. FIG. 2C shows a fully inflated balloon which has been detached from the catheter 28, such that the catheter 28 and needle 26 can be withdrawn from the implant site.

Figure 3A:
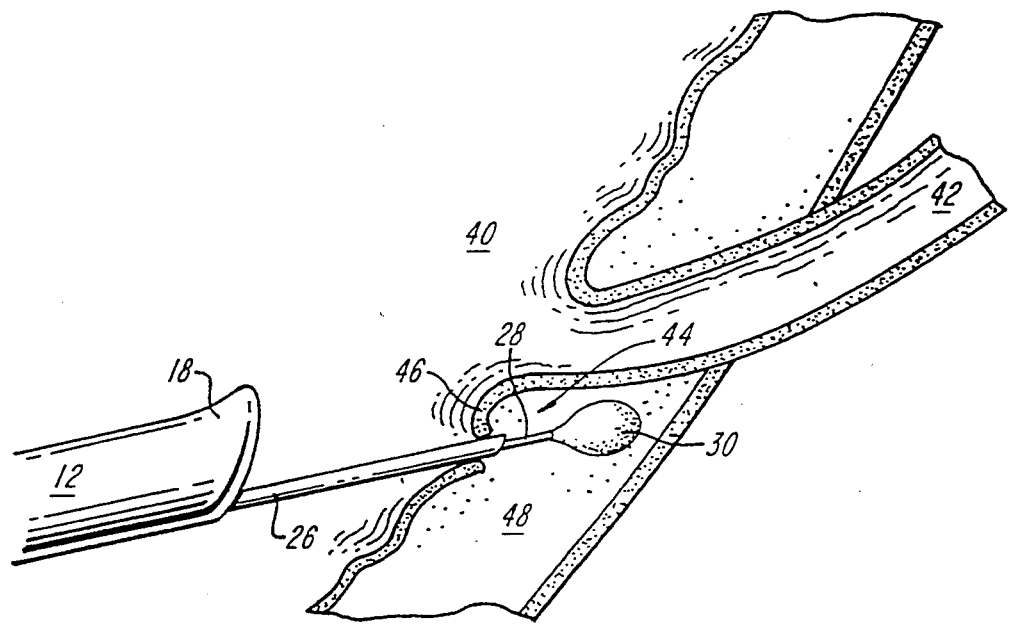
FIG. 3A is a schematic diagram illustrating an initial stage of a method according to the invention in which a pocket is established within the subureteral region.

In use, the invention can be practiced by introducing the cystoscope 12 into the bladder 40 and, as shown in FIG. 3A, inserting the needle 26 into the subureteral region of the refluxing ureter 44 (e.g. between the mucosal and submucosal tissue layers 46, 48, respectively). The balloon 30 with the attached delivery catheter 28 then is inserted through the core of the needle 26 and placed in the subureteral region. After inflation of the balloon, e.g., with a polymerizable solution, the needle is withdrawn from the subureteral tissue leaving the balloon in place.

Figure 3B:
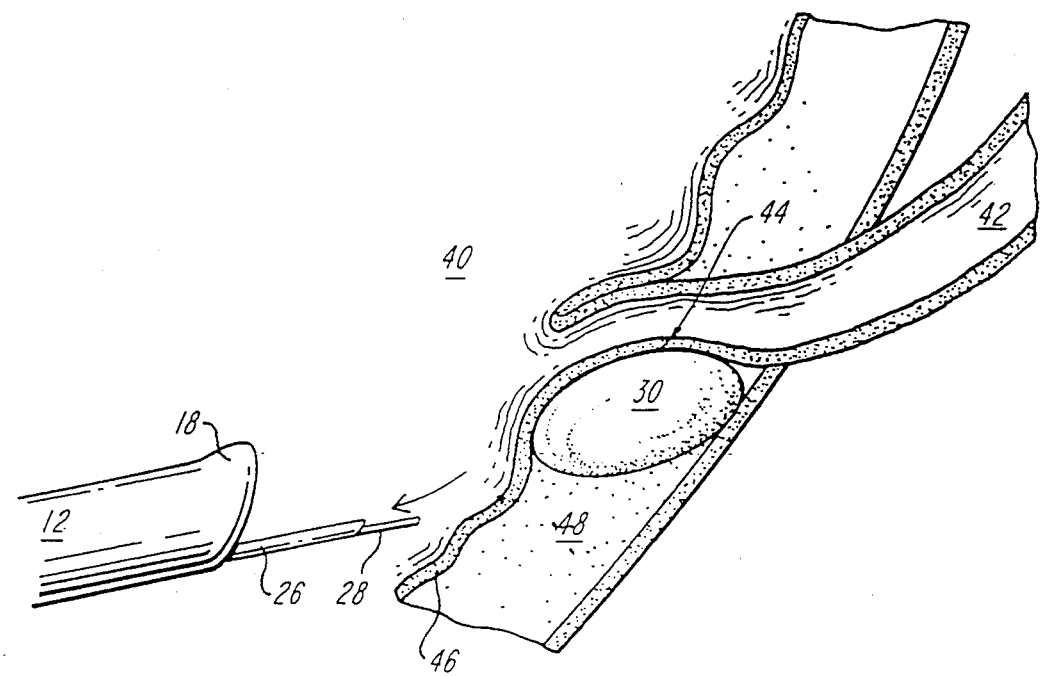
FIG. 3B is a further schematic diagram illustrating a subsequent stage in the method of FIG. 3A in which a balloon is inflated within the pocket and then detached.

Hydroxyethyl methylacrylate (HEMA), a hydrophylic polymer compatible with silicone and which solidifies within 60 minutes after the addition of ferrous sulfate and hydrogen peroxide, is particularly useful as a filling material for the balloon 30. HEMA can be injected through the catheter 28 to inflate the balloon 30, while endoscopically visualizing the balloon compressive effect on its surrounding tissue. The catheter is then pulled, leaving the self-sealing detachable balloon in place, as shown in FIG. 3B. The compressive effect of the inflated balloon 30 is to reconfigure the ureteral tunnel 44 so as to minimize the likelihood of reflux.

The invention will next be described in connection with certain non-limiting experimental protocols.

EXAMPLES

A system similar to that shown in FIG. 1 was constructed with catheter having a length of about 100 centimeters and the diameter of about 2.0 French. The balloon design included a small lip seal valve closure mechanism and had an uninflated diameter of about 0.034 inches. A thin walled cystoscopic needle was obtained from Cook Urological (Spencer, Ind.) which had a 19 gauge outer diameter but had the inner diameter of a standard 18 gauge needle (0.036 inches). HEMA was used as the filling material for the balloons. Infused through the deliver catheter and into the balloon HEMA progresses from a water like liquid state, to a semi-solid gel form and ultimately solidifies within the balloon shell. Polymerization time is controlled by varying the ingredients necessary for the reaction to occur. An estimated time to cure of 60 minutes was achieved by utilizing a solution composed of 4.5% of HEMA, 32.2% of hydrogen peroxide and 3.25% of ferrous ammonium sulfate.

Pigs were chosen for this study because of the similarities between porcine and human kidneys. The Hanford minipig was used for the convenience of its smaller size. Preoperative intravenous pyelograms (IVP's) and cystograms with Conray (Mallinkrodt, Inc., St. Louis, Mo.) were performed in 5 of the 6 minipigs.

Reflux was created in 6 female Hanford minipigs by unroofing the ureters bilaterally. This was done with the standard technique of open surgery in two minipigs. However in the other 4 we attempted and were successful in creating reflux endoscopically utilizing laparoscopic scissors through a 14 French cystoscope.

Four to 6 weeks later the presence of bilateral reflux was confirmed with a cystogram and the balloon was implanted unilaterally in the subureteral region. This was done with open surgery in the first minipig and endoscopically through a 19 gauge needle and a 15 Fr. cystoscope in 5 minipigs. A repeat cystogram and IVP were performed 2 to 4 weeks after implantation.

Serial cystograms, ultrasounds, and IVP's were performed at 4 to 6 week intervals until sacrifice. The six minipigs were sacrificed at 4(1), 8(2), 12(2), and 24(1) weeks after balloon implantation. The bladder balloon implant sites were resected and analyzed macroscopically and microscopically. Histologic analyses of the bladder, ureters, regional lymph nodes, kidneys, spleen, liver and the tissue surrounding the balloon implant sites were performed.

All minipigs which had preoperative studies had no evidence of reflux as demonstrated by a cystogram and no evidence of obstruction as demonstrated by ultrasonography or IVP's. Four to six weeks after unroofing the ureters bilaterally, cystograms confirmed the presence of bilateral reflux, and IVP's and renal ultrasonography demonstrated no evidence of obstruction in each animal.

Cystography was again performed 2 to 4 weeks after balloon implantation in all animals. This demonstrated resolution of reflux in the treated ureter and persistence of reflux in the opposite untreated ureter. The serial cystograms, ultrasounds, and IVP's performed at 4 to 6 week intervals showed persistence of reflux in the untreated side and continued effectiveness of the balloon in the implanted ureter without reflux or evidence of obstruction.

After sacrifice, gross inspection of the bladder implant site showed no evidence of extrusion or abscess formation in any of the minipigs. Microscopic analyses of the tissues surrounding the balloon implant showed mild inflammation. A fibrotic reaction was also evident between the balloon shell and the ureteral tissue. Tissue sections from the lymph nodes, kidneys, liver and spleen showed no evidence of particle migration or inflammatory reaction.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A directly, visualized method for deploying a detachable balloon to a target site in vivo, comprising:
    providing a scope for directly visualizing a target site in vivo, the scope comprising a sheath a viewing means for viewing the target site and a positioning element extending longitudinally through the sheath;
    passing an uninflated, detachable balloon attached to a catheter through a lumen of a positioning element of the scope to a target site in vivo; and
    inflating and detaching the balloon at the target site in vivo while directly visualizing the detachment of the balloon and/or the effects of the detached balloon on the target site in vivo.

2. The method of claim 1 wherein the positioning element is a hypodermic needle.

3. The method of claim 1 wherein the lumen of the positioning element has an inside diameter of less than about 0.036 inches.

4. The method of claim 1 wherein the detachable balloon is inflated with a biocompatible material.

5. The method of claim 1 wherein the detachable balloon is inflated with a polymerizable solution which gels or solidifies in vivo.

6. The method of claim 1 wherein the target site in vivo in the passing step is selected such that the detached, inflated balloon provides occlusive pressure to a duct.

7. The method of claim 1 wherein the target site in vivo in the passing step is selected such that the detached, inflated balloon provides blockage within a duct.

8. The method of claim 7 where the blockage within the duct is complete blockage.

9. The method of claim 1 wherein the target site in vivo in the passing step is the subureteral region of a reflux-prone bladder.

10. The method of claim 1 wherein the target site in vivo in the passing step is selected to cause blockage or closure of fallopian tubes in a female subject.

11. The method of claim 1 wherein the target site in vivo in the passing step is between the urethra and the subcutaneous corpus spongiousum.

12. The method of claim 1 wherein the target site in vivo in the passing step is selected to cause blockage or closure of a duct involved in the delivery of sperm outside the body of a male subject.

13. A system for deploying a detachable balloon to a target site in vivo and directly visualizing the detached, inflated balloon and/or its effects in vivo, comprising:
    a scope for directly visualizing a target site in vivo, the scope comprising a shealth, a viewing means for viewing a target site and a positioning element extending longitudinally through the sheath; and
    a balloon catheter including a detachable, uninflated balloon, said detachable, uninflated balloon adapted for passage through a lumen of the positioning element of the scope.

14. The system of claim 13 wherein the positioning element of the scope is a hypodermic needle.

15. The system of claim 13 wherein the lumen of the positioning element of the scope has an inside diameter of less than about 0.036 inches.

16. The system of claim 13 wherein the scope includes an endoscope.

17. The system of claim 16 wherein the scope includes a cystoscope.

18. The system of claim 13 wherein the balloon catheter comprises a sealing means for sealing the balloon following inflation.

19. The system of claim 18 wherein the sealing means comprises a constrictive collar.

20. The system of claim 18 wherein the sealing means comprises a hip seal.

21. The system of claim 13 wherein the detachable balloon is a silicone rubber balloon.

* * * * *